United States Patent [19]

Yoshida et al.

[11] Patent Number: 5,269,813
[45] Date of Patent: Dec. 14, 1993

[54] MATERIAL FOR ONE-PIECE INTRAOCULAR LENSES

[75] Inventors: Kunihisa Yoshida; Kazuhiko Nakada, both of Aichi, Japan

[73] Assignee: Menicon Co., Ltd., Nagoya, Japan

[21] Appl. No.: 712,278

[22] Filed: Jun. 10, 1991

[30] Foreign Application Priority Data

Jun. 12, 1990 [JP] Japan .................. 2-153060
Aug. 25, 1990 [JP] Japan .................. 2-223779

[51] Int. Cl.⁵ .................. A61F 2/16; G02B 1/04
[52] U.S. Cl. .................. 623/6; 523/106; 526/245; 526/328.5; 526/329.4; 526/329.5; 526/329.7
[58] Field of Search .......... 523/106; 526/328.5, 526/329.4, 329.7, 245, 329.5; 623/6

[56] References Cited

U.S. PATENT DOCUMENTS

| | | | |
|---|---|---|---|
| 4,605,717 | 8/1986 | Heitner | 526/329.5 |
| 4,713,412 | 12/1987 | Czerepinski et al. | 526/328.5 |
| 4,731,079 | 3/1988 | Stoy | 623/6 |
| 4,834,750 | 5/1989 | Gupta | 623/6 |
| 4,904,421 | 2/1990 | Ando et al. | 523/106 |
| 4,946,470 | 8/1990 | Sulc et al. | 523/106 |

FOREIGN PATENT DOCUMENTS

| | | | |
|---|---|---|---|
| 151762 | 8/1985 | European Pat. Off. | |
| 269288 | 6/1988 | European Pat. Off. | |
| 336318 | 10/1989 | European Pat. Off. | |
| 379146 | 7/1990 | European Pat. Off. | |
| 0026014 | 2/1985 | Japan | 526/328.5 |
| 60-170610 | 4/1985 | Japan | |
| 87-166211 | 10/1985 | Japan | |
| 1141714 | 6/1986 | Japan | 526/329.5 |
| 3072706 | 4/1988 | Japan | 526/245 |
| 2199672 | 7/1988 | United Kingdom | |

*Primary Examiner*—Paul R. Michl
*Assistant Examiner*—Andrew E. C. Merriam
*Attorney, Agent, or Firm*—Armstrong, Westerman, Hattori, McLeland & Naughton

[57] ABSTRACT

A material for one-piece intraocular lenses containing a copolymer whose main components are methyl methacrylate and at least one (meth)acrylate selected from an alkyl acrylate having a glass transition temperature of higher than 30° C. and up to 100° C. and a fluoroalkyl (meth)acrylate having a glass transition temperature of higher than 30° C. and up to 100° C. This material for one-piece intraocular lenses has excellent cutting-processability, grindability, machinability and suitable flexibility, and can be suitably used for not only one-piece intraocular lenses but also three-piece intraocular lenses.

5 Claims, No Drawings

MATERIAL FOR ONE-PIECE INTRAOCULAR LENSES

BACKGROUND OF THE INVENTION

The present invention relates to a material for one-piece intraocular lenses.

Intraocular lenses are composed of a lens body and a haptic. The intraocular lenses are mainly classified into one-piece intraocular lenses of which lens body is formed integrally with a haptic and three-piece intraocular lenses produced by assembling a lens body and a haptic which are manufactured separately from each other.

As the material of the one-piece intraocular lens, a hard-type material composed of a hard material such as polymethyl methacrylate, and a soft-type material composed of a soft material such as a silicone rubber not having water-absorptive property or poly(2-hydroxyethyl methacrylate) having water-absorptive property are known.

One-piece intraocular lenses composed of a hard-type material such as polymethyl methacrylate have some advantages that include excellent positioning in eyes, stability for visual acuity and biocompatibility and little degradation in human eyes. However the intraocular lenses have some disadvantages, which include that the lenses cannot be easily inserted into eyes on operation because the haptic has small flexibility, and that the haptic is easily broken during the implantation of the intraocular lens in eyes because its flexural strength is small.

Also, one-piece intraocular lenses composed of a soft-type material have some advantages that the one-piece intraocular lenses mechanically little damage the tissues of eyes even though the intraocular lenses are touched to a corneal endothelium or an iris during their insertion in eyes since the intraocular lenses are generally soft. However, their positioning is insufficient since the haptic is soft, and therefore, the intraocular lenses are easily slidden or defected and visual acuity is apt to be unstable.

Accordingly, as a one-piece intraocular lens dissolving the above-mentioned defects, an intraocular lens not having water-absorptive property and having suitable flexibility and excellent mechanical strength has been developed (Japanese Unexamined Patent Publication No. 97559/1987 and Japanese Unexamined Patent Publication No. 158949/1989).

The intraocular lenses described in the above-mentioned publications surely do not have water-absorptive property and have suitable flexibility and excellent mechanical strength, but it is difficult to polish its material to give an intraocular lens having a desired lens shape by means of conventional polishing methods. Therefore, the improvement of mechanical processability has been expected.

It is an object of the present invention to provide a material for one-piece intraocular lenses having a hard optical portion and a haptic having suitable elasticity.

It is another object of the present invention to provide a material for one-piece intraocular lenses having excellent cutting processabity as well as excellent positioning in eyes.

These and other objects of the present invention will become apparent from the description hereinafter.

SUMMARY OF THE INVENTION

In accordance with the present invention, there is provided a material for one-piece intraocular lenses consisting essentially of a copolymer of which main components are methyl methacrylate and at least one (meth)acrylate selected from an alkyl (meth)acrylate having a glass transition temperature of higher than 30° C. and up to 100° C. and a fluoroalkyl (meth)acrylate having a glass transition temperature of higher than 30° C. and up to 100° C.

DETAILED DESCRIPTION

The material for one-piece intraocular lenses of the present invention has a characteristic in that at least one of an alkyl (meth)acrylate and a fluoroalkyl (meth)acrylate having a glass transition temperature of higher than 30° C. and up to 100° C. is used as a monomer for a copolymer constituting the material of one-piece intraocular lenses aforementioned above. Since such a monomer is used in the copolymer, the material of the intraocular lenses having a hard optical portion and a haptic having suitable elasticity and giving positioning can be provided although the optical portion and the haptic are made of a single material.

Accordingly, since the material for one-piece intraocular lenses of the present invention has suitable flexibility, an intraocular lens can be easily inserted in eyes in a state that the incision of a bulbus oculi is small. In addition, since the material for one-piece intraocular lenses of the present invention has suitable mechanical strength, the material is excellent in cutting processability, in particular polishing property.

The material for one-piece intraocular lenses of the present invention having suitable flexibility and mechanical strength and exhibiting sufficient positioning can be suitably used not only as a material for one-piece intraocular lenses but also as a material for three-piece intraocular lenses.

The material for one-piece intraocular lenses of the present invention consisting essentially of a copolymer of which main components are methyl methacrylate (hereinafter referred to as MMA) and at least one (meth)acrylate selected from an alkyl (meth)acrylate having a glass transition temperature of higher than 30° C. and up to 100° C. (hereinafter referred to as alkyl (meth)acrylate and a fluoroalkyl (meth)acrylate having a glass transition temperature of higher than 30° C. and up to 100° C. (hereinafter referred to as fluoroalkyl (meth)acrylate).

The MMA used in the present invention is excellent in biocompatibility and little degradation in human eyes, and also gives excellent dimensional stability.

The amount of the above-mentioned MMA is 53 to 95 parts (parts by weight, hereinafter referred to the same), preferably 55 to 95 parts based upon 100 parts of the components for a copolymer. When the amount of the MMA is less than the above-mentioned range, sufficient hardness endurable for mechanical processing, which is carried out when producing an intraocular lens, is not imparted to the material. When the amount of the MMA exceeds the above-mentioned range, although the obtained material possesses desirable hardness for a optical material, there is a tendency that the material does not have the elasticity necessary for a haptic.

The alkyl (meth)acrylate and the fluoroalkyl (meth)acrylate used in the present invention are the components for imparting desirable elasticity necessary for a haptic to an obtained material for one-piece intraocular lenses. In the present invention, the reason why it is necessitated that each of the glass transition temperatures of the above-mentioned alkyl (meth)acrylate and fluoroalkyl (meth)acrylate is higher than 30° C. and up to 100° C. is to obtain a lens material for one-piece intraocular lenses having suitable flexibility, which can be polished.

There is a necessity that the glass transition temperature of an obtained material is 70° to 105° C. so that the material can have suitable flexibility and can be polished. Therefore, each of the transition temperatures of the above-mentioned alkyl (meth)acrylate and fluoroalkyl (meth)acrylate is preferably at least 40° C., and more preferably from 50° to 95° C.

Concrete examples of the above-mentioned alkyl (meth)acrylate are, for instance, t-butyl acrylate (glass transition temperature: 43° C.), 2-t-butylphenyl acrylate (glass transition temperature: 72° C.), naphthyl acrylate (glass transition temperature: 85° C.), 4-methoxyphenyl acrylate (glass transition temperature: 51° C.), 2-methoxycarbonylphenyl acrylate (glass transition temperature: 46° C.), 2-chlorophenyl acrylate (glass transition temperature: 53° C.), 4-chlorophenyl acrylate (glass transition temperature: 58° C.), 2-cyanobenzyl acrylate (glass transition temperature: 44° C.), 4-cyanophenyl acrylate (glass transition temperature: 90° C.), isobornyl acrylate (glass transition temperature: 94° C.), ethyl methacrylate (glass transition temperature: 65° C.), propyl methacrylate (glass transition temperature: 35° C.), isopropyl methacrylate (glass transition temperature: 81° C.), sec-butyl methacrylate (glass transition temperature: 60° C.), isobutyl methacrylate (glass transition temperature: 53° C.), cyclohexyl methacrylate (glass transition temperature: 83° C.), benzyl methacrylate (glass transition temperature: 54° C.), 2-cyanoethyl methacrylate (glass transition temperature: 91° C.), and the like. These alkyl (meth)acrylates are usually used alone or in admixture thereof.

Concrete examples of the above-mentioned fluoroalkyl (meth)acrylate are, for instance, trifluoroethyl methacrylate (glass transition temperature: 80° C.), hexafluoroisopropyl methacrylate (glass transition temperature: 95° C.), tetrafluoropropyl methacrylate (glass transition temperature: 75° C.), octafluoropentyl methacrylate (glass transition temperature: 36° C.), and the like. These fluoroalkyl (meth)acrylates are usually used alone or in admixture thereof.

In the present invention, the above-mentioned alkyl (meth)acrylate and fluoroalkyl (meth)acrylate are used alone respectively or in admixture thereof, Among these alkyl (meth)acrylates and fluoroalkyl (meth)acrylates, alkyl (meth)acrylates are particularly preferably used because refractive index of an obtained material for one-piece intraocular lenses can be kept high.

The amount of the above-mentioned (meth)acrylate selected from the alkyl (meth)acrylate and the fluoroalkyl (meth)acrylate is 5 to 47 parts, preferably 5 to 45 parts based upon 100 parts of the components for a copolymer. When the amount is less than the above-mentioned range, although an obtained material has desirable hardness as an optical material, the material does not have elasticity necessary for a haptic. When the amount exceeds the above-mentioned range, there is a tendency that sufficient hardness endurable for mechanical processing, which is carried out when an intraocular lens having a desirable lens shape is produced, is not imparted to the material.

Since the material for one-piece intraocular lenses of the present invention comprises the above-mentioned components, its glass transition temperature can be maintained between 70° to 105° C. The preferable glass transition temperature is 80° to 105° C. When the glass transition temperature is lower than 70° C., an obtained material shows rubber-like elasticity in eyes (having a temperature of about 37° C.), and therefore, the positioning of a haptic is insufficient and it is difficult to ground the material, and further such a problem that the generation of deformation of a lens is caused when an obtained one-piece intraocular lens is subjected to thermal treatment in a sterilization process after the one-piece intraocular lens is produced. When the glass transition temperature is higher than 105° C., since an obtained material has a property similar to polymethyl methacrylate (glass transition temperature: 112° C.) solely, and suitable flexibility cannot be imparted to the material, it is apt to occur some problems that it is difficult to insert an obtained intraocular lens into eyes, in particular at the portion of a haptic, and that the haptic is easily broken during implantation in eyes.

The material for one-piece intraocular lenses of the present invention is prepared by polymerizing components for a copolymer, of which main components are the MMA and at least one selected from the alkyl (meth)acrylate and the fluoroalkyl (meth)acrylate. However, so long as the objects of the present invention are not prevented, the other components can be used in the components for a copolymer.

In the present invention, in case a material for one-piece intraocular lenses having high solvent resistance and excellent shape stability is required, a crosslinking agent can be used.

Examples of the above-mentioned crosslinking agent are, for instance, ethyleneglycol dimethacrylate, allyl methacrylate, trimethylolpropane trimethacrylate, divinylbenzeneallyl phthalate, and the like. These are used alone or in admixture thereof.

The amount of the above-mentioned crosslinking agent is usually adjusted so that the amount does not exceeds 10 parts based upon 100 parts of the components for a copolymer. When the amount exceeds 10 parts, an obtained material for one-piece intraocular lenses tends to be brittle.

In the present invention, a radical polymerization initiator which is usually used in polymerization of unsaturated hydrocarbons can be used in polymerization of the above-mentioned components for a copolymer.

Concrete examples of the above-mentioned radical polymerization initiator are, for instance, benzoylperoxide, azobisisobutyronitrile, azobisdimethylvaleronitrile, and the like. These are used alone or in admixture thereof.

The amount of the above-mentioned radical polymerization initiator is usually adjusted so that the amount is 0.01 to 1 part or so based upon 100 parts of the components for a copolymer. When the amount is less than 0.01 part, polymerization reaction is too low, and when the amount exceeds 1 part, there is a tendency that bubbles are produced in an obtained material for one-piece intraocular lenses.

In the present invention, an ultraviolet absorber, a coloring agent and the like can be furthermore contained in the material as occasion demands.

Concrete examples of the above-mentioned ultraviolet absorber are, for instance, benzophenones such as 2-hydroxy-4-methoxybenzophenone and 2-hydroxy-4-octoxybenzophenone; benzotriazoles such as 2-(2'-hydroxy-5'-methylphenyl)benzotriazole and 5-chloro-2(3'-t-butyl-2'-hydroxy-5'-methylphenyl)-benzotriazole; salicylic acid derivatives; hydroxyl acetophenones, and the like. Also, a reactive ultraviolet absorber both having a chemical structure similar to these ultraviolet absorbers and being copolymerizable with the components for a copolymer according to the present invention can be used. These can be used alone or in admixture thereof. To correct the cyanopsia of a patient not having a crystalline lens after implantation ot the intraocular lens, it is desirable that the above-mentioned coloring agent has yellow to orange color. Concrete examples of the coloring agent are, for instance, oil-soluble dyes such as CI Solvent Yellow and CI Solvent Orange which are described in Color Index (CI); dispersed dyes such as CI Disperse Yellow, and CI Disperse Orange; vat dyes, and the like. Reactive coloring agents both having a chemical structure similar to these coloring agents and being copolymerizable with the components for a copolymer according to the present invention also can be used. These can be usually used alone or in admixture thereof.

Each amount of the ultraviolet absorber agent and the coloring agent is usually adjusted so that each amount of them does not exceed 5 parts or so based upon 100 parts of the components for a copolymer.

As a method for copolymerizing the components for a copolymer and a molding method for producing a material for one-piece intraocular, lenses according to the present invention, conventional copolymerization techniques and molding techniques can be employed. For instance, the above-mentioned components for a copolymer can be copolymerized in a prescribed mold so that an intraocular lens can be easily produced and then an obtained material can be cut and processed to give an intraocular lens having a shape corresponding to an intraocular lens, and the above-mentioned components also can be previously copolymerized and molded in a mold having a shape corresponding to an intraocular lens. The present invention is not limited to the above exemplified copolymerization methods and molding methods.

Further, an obtained material for intraocular lenses can be naturally subjected to cutting, polishing, and the like.

When the above-mentioned components for a copolymer are copolymerized in a mold, as a mold, for instance, a mold made of glass, polyethylene, polypropylene or the like can be used.

The thus obtained material for one-piece intraocular lenses can be suitably used, for instance, for one-piece intraocular lenses of which lens body is formed integrally with a haptic.

The present invention is more specifically described and explained by means of the following Examples. It is to be understood that the present invention is not limited to the Examples, and various changes and modifications may be made in the invention without departing from the spirit and scope thereof.

EXAMPLES 1 TO 11 AND COMPARATIVE EXAMPLE 1

The MMA, an alkyl (meth)acrylate, a fluoroalkyl (meth)acrylate, a crosslinking agent and a polymerization initiator were admixed together to give a composition shown in Table 1.

The composition was poured into a tubular glass mold having an inside diameter of 15 mm and a depth of 500 mm. The polymerization reaction was carried out in the mold on a water bath having a water temperature of 35° C. for 40 hours and then 50° C. for 6 hours.

After the polymerization reaction was finished, the mold was taken out from the water bath, and placed in an oven. After the mold was heated for each 10° C. rise in temperature from 50° to 130° C. keeping each temperature for 1.5 hours, the mold was allowed to stand to cool to room temperature. A material for one-piece intraocular lenses was taken out from the mold.

As the physical properties of the obtained material for one-piece intraocular lenses, refractive index, hardness, machanical processability, elasticity, appearance and glass transition temperature were examined in accordance with the following methods. The results are shown in Table 1.

Method for Measuring the Physical Properties of the Obtained Material for One-Piece Intraocular Lenses (A) Refractive index The obtained material for one-piece intraocular lenses was processed to give a test piece having a diameter of 13 mm and a thickness of 5 mm. The refractive index was measured in accordance with Japanese Industrial Standards (JIS) K-7105.

(B) Hardness

After the obtained material for one-piece intraocular lenses was processed to give a test piece having a diameter of 13 mm and a thickness of 5 mm, shore hardness D was measured in accordance with the method prescribed in ASTM D-2240.

(C) Mechanical processability

The obtained material was processed to the shape of a one-piece intraocular lens by means of a computer aided modeling machine. When the material could be processed accurately to a desired shape, it was judged as "Good". When the material could not be processed, it was judged as "Not Good".

(D) Elasticity

One-piece intraocular lenses produced in the above item "(C) mechanical processability" were used. After the optical portion of the lens was gripped in a vise so that the optical portion could not be moved, the end of the haptic of the lens was held by a pincette for operation. The end of the haptic was bent 100 times to the optical portion.

After that, the one-piece intraocular lens was observed by means of a magnifier (×10). When no charge was observed in comparison with the lens before the test, it was decided as "Good", and when change was observed, it was decided as "Not Good".

(E) Appearance

The appearance of each obtained materials was observed with naked eyes.

(F) Glass transition temperature

After the obtained material for one-piece intraocular lenses was processed to give a test piece having a diameter of 4 mm and a thickness of 0.15 mm, the glass transition temperature of the test piece was measured by means of SSC5200 and DSC220C which were commercially available from Seiko Instruments Inc.

As the conditions for measuring the glass transition temperature, the range of the temperature was adjusted to room temperature to 150° C., and the temperature gradient was adjusted to 10° C./min.

TABLE 1

| Ex. No. | Components (parts) | | | | | Physical properties of material for one-piece intraocular lenses | | | | | |
|---|---|---|---|---|---|---|---|---|---|---|---|
| | MMA | Alkyl (meth)-acrylate | Fluoro-alkyl (meth)-acrylate | Cross-linking agent | Polymer-ization initiator | Reflac-tive index | Hard-ness (Shore D) | Mechanical process-ability | Elas-ticity | Appear-ance | Glass tran-sition tempera-ture (°C.) |
| 1 | 87 | EMA*¹ 10 | — | EDMA*⁶ 3 | AIBN*⁷ 0.1 | 1.490 | 91 | Good | Good | Transparent | 101 |
| 2 | 70 | EMA 30 | — | — | AIBN 0.1 | 1.488 | 89 | Good | Good | Transparent | 93 |
| 3 | 47 | EMA 60 | — | EDMA 3 | AIBN 0.1 | 1.487 | 89 | Good | Good | Transparent | 85 |
| 4 | 70 | i-BuMA*² 30 | — | — | AIBN 0.1 | 1.484 | 89 | Good | Good | Transparent | 89 |
| 5 | 54 | — | 3FE*³ 45 | EDMA 1 | AIBN 0.1 | 1.457 | 89 | Good | Good | Transparent | 94 |
| 6 | 68 | — | 4FP*⁴ 30 | EDMA 2 | AIBN 0.1 | 1.473 | 90 | Good | Good | Transparent | 96 |
| 7 | 67 | — | 6FP*⁵ 30 | EDMA 3 | AIBN 0.1 | 1.461 | 90 | Good | Good | Transparent | 102 |
| 8 | 52 | EMA 30 | 3FE 15 | EMDA 3 | AIBN 0.1 | 1.477 | 89 | Good | Good | Transparent | 89 |
| 9 | 77 | EMA 15 | 3FE 5 | EDMA 3 | AIBN 0.1 | 1.486 | 91 | Good | Good | Transparent | 98 |
| 10 | 67 | EMA 25 | 3FE 5 | ADMA 3 | AIBN 0.1 | 1.485 | 90 | Good | Good | Transparent | 94 |
| 11 | 67 | EMA 15 | 3FE 15 | EDMA 3 | AIBN 0.1 | 1.478 | 90 | Good | Good | Transparent | 95 |
| Com. Ex. 1 | 100 | — | — | — | AIBN 0.1 | 1.492 | 91 | Not Good | Good | Transparent | 112 |

(Notes)
*¹Ethyl methacrylate,
*²Isobutyl methacrylate,
*³Trifluoroethyl methacrylate,
*⁴Tetrafluoropropyl methacrylate,
*⁵Hexafluoroisopropyl methacrylate,
*⁶Ethyleneglycol dimethacrylate,
*⁷Azobisisobutylonitrile As is clear from the results shown in Table 1, it can be seen that the one-piece intraocular lenses obtained in Examples 1 to 11 of the present invention have excellent transparency, hardness and mechanical processability as well as conventional intraocular lenses made of polymethyl methacrylate, and have elasticity suitable for a haptic at the same time.

The material for one-piece intraocular lenses of the present invention has transparency required for one-piece intraocular lenses, suitable hardness, elasticity and mechanical strength, and is excellent in mechanical processability such as cutting and polishing. Therefore, the material can be suitably used in particular for one-piece intraocular lenses.

Also, since the material for one-piece intraocular lenses consists essentially of a copolymer containing the MMA which is said that the polymethyl methacrylate is excellent in biocompatibility and little degradation in human eyes, the material is excellent in biocompatibility and exhibits little degradation in human eyes.

In addition to the ingredients used in the Examples, other ingredients can be used in the Examples as set forth in the specification to obtain substantially the same results.

What is claimed is:

1. A one-piece intraocular lens made of a copolymer consisting essentially of:

(A) methyl methacrylate,
   (B) a fluoroalkyl (meth)acrylate having a glass transition temperature of higher than 30° C. and up to 100° C., and
   (C) a crosslinking agent, wherein a glass transition temperature of said copolymer is 70° to 105° C.

2. The one-piece intraocular lens of claim 1, wherein said crosslinking agent is a member selected from the group consisting of ethyleneglycol dimethacrylate, allyl methacrylate, trimethylolpropane trimethacrylate and divinylbenzeneallyl phthalate.

3. A one-piece intraocular lens made of a copolymer consisting essentially of:

(A) methyl methacrylate,
   (B) an alkyl (meth)acrylate having a glass transition temperature of higher than 30° C. and up to 100° C.,
   (C) a fluoroalkyl (methacrylate having a glass transition temperature of higher than 30° C. and up to 100° C., and
   (D) a crosslinking agent, wherein a glass transition temperature of said copolymer is 70° to 105° C.

4. The one-piece intraocular lens of claim 3, wherein said alkyl (meth)acrylate is ethyl methacrylate.

5. The one-piece intraocular lens of claim 3, wherein said crosslinking agent is a member selected from the group consisting of ethyleneglycol dimethacrylate, allyl methacrylate, trimethylolpropane trimethacrylate and divinylbenzeneallyl phthalate.

* * * * *